(12) United States Patent
Haras

(10) Patent No.: US 9,078,960 B2
(45) Date of Patent: Jul. 14, 2015

(54) CONTROL APPARATUS FOR A MEDICAL EXAMINATION APPARATUS

(75) Inventor: Gabriel Haras, Mücke (DE)

(73) Assignee: Siemens Aktiengesellschaft, Munich (DE)

( * ) Notice: Subject to any disclaimer, the term of this patent is extended or adjusted under 35 U.S.C. 154(b) by 1699 days.

(21) Appl. No.: 11/826,439

(22) Filed: Jul. 16, 2007

(65) Prior Publication Data

US 2008/0033289 A1  Feb. 7, 2008

(30) Foreign Application Priority Data

Jul. 17, 2006  (DE) .......................... 10 2006 032 954

(51) Int. Cl.
| | | |
|---|---|---|
| *A61M 37/00* | (2006.01) | |
| *A61B 6/00* | (2006.01) | |
| *A61M 5/172* | (2006.01) | |
| *A61M 5/00* | (2006.01) | |
| *A61M 5/142* | (2006.01) | |

(52) U.S. Cl.
CPC ................ *A61M 5/007* (2013.01); *A61B 6/481* (2013.01); *A61M 5/172* (2013.01); *A61B 6/507* (2013.01); *A61M 2005/14208* (2013.01)

(58) Field of Classification Search
CPC ....... A61B 6/481; A61B 6/507; A61M 5/172; A61M 5/007; A61M 2005/14208
USPC ........................ 600/431, 432, 420; 604/131
See application file for complete search history.

(56) References Cited

U.S. PATENT DOCUMENTS

| | | | |
|---|---|---|---|
| 6,195,579 B1 * | 2/2001 | Carroll et al. ................. | 600/420 |
| 6,397,097 B1 | 5/2002 | Requardt | |
| 2004/0202358 A1 * | 10/2004 | Breeuwer ...................... | 382/128 |
| 2005/0187465 A1 * | 8/2005 | Motomura et al. ........... | 600/428 |
| 2006/0074286 A1 * | 4/2006 | Miller et al. .................. | 600/407 |
| 2006/0074305 A1 * | 4/2006 | Mostafavi ..................... | 600/428 |
| 2008/0009696 A1 * | 1/2008 | Hempel ........................ | 600/407 |
| 2008/0306381 A1 * | 12/2008 | Feuerlein et al. ............. | 600/425 |

FOREIGN PATENT DOCUMENTS

DE  19811349 C1  10/1999

OTHER PUBLICATIONS

Bae, Kyongtae T. "Intravenous Contrast Medium Administration and Scan Timing at CT: Considerations and Approaches". Radiology: vol. 256, No. 1, Jul. 2010. pp. 32-61.*

* cited by examiner

*Primary Examiner* — Long V Le
*Assistant Examiner* — Angela M Hoffa
(74) *Attorney, Agent, or Firm* — Harness, Dickey & Pierce

(57) ABSTRACT

A control apparatus is disclosed, for a medical examination apparatus, for controlling a first injection of contrast agent for an examination, a breathing command and a recording of an examination image of an examination area of a patient after a circulation time has elapsed. In at least one embodiment, the control apparatus includes a control unit for controlling the start of the injection after the start of the breathing command. This makes it possible to provide reliable evaluation capability for the examination images that are produced, even for examinations with a circulation time which is short in comparison to the breathing command, for example perfusion examinations.

9 Claims, 1 Drawing Sheet

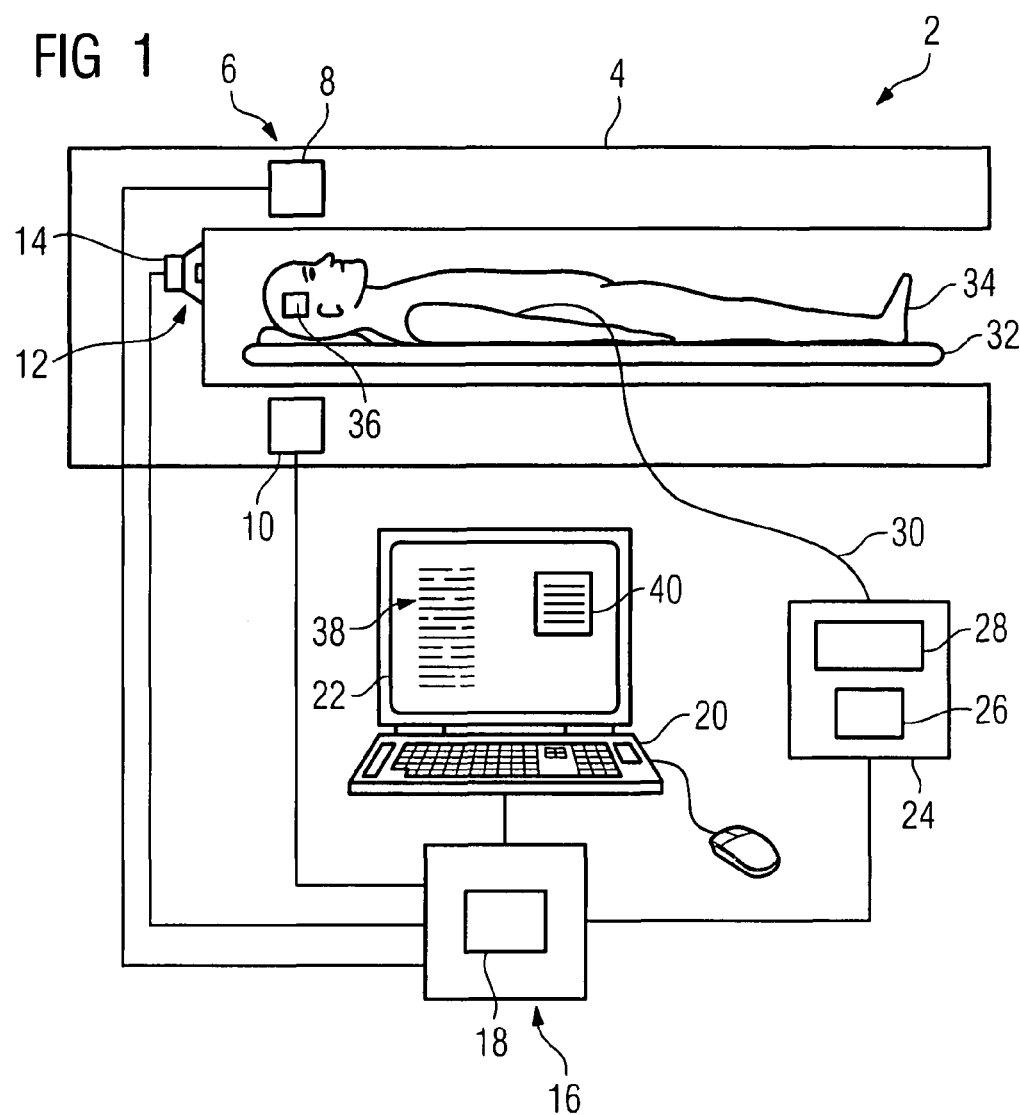
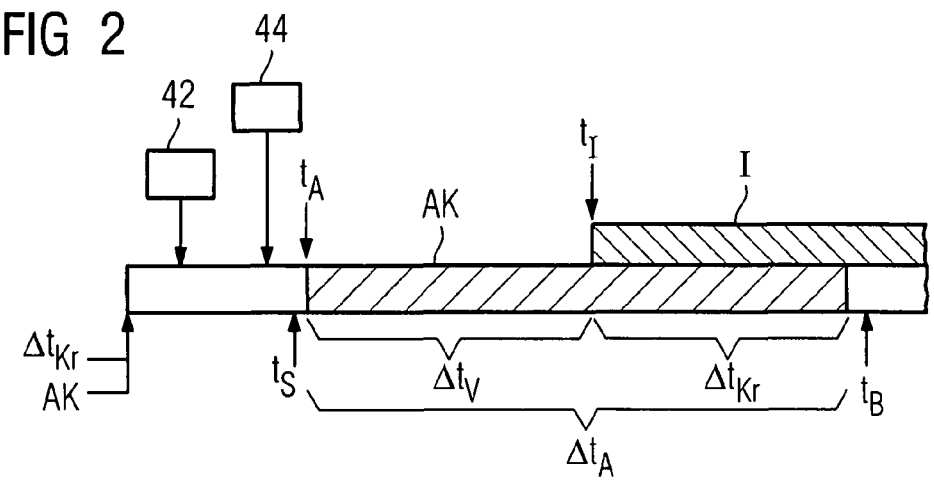

CONTROL APPARATUS FOR A MEDICAL EXAMINATION APPARATUS

PRIORITY STATEMENT

The present application hereby claims priority under 35 U.S.C. §119 on German patent application number DE 10 2006 032 954.6 filed Jul. 17, 2006, the entire contents of which is hereby incorporated herein by reference.

FIELD

Embodiments of the invention generally relate to a control apparatus for a medical examination apparatus, such as one, for example, for controlling a first injection of contrast agent for an examination, a breathing command and a recording of an examination image of an examination area of a patient after a circulation time has elapsed.

BACKGROUND

In the case of imaging medical examination processes, such as computed tomography (CT), magnet resonance processes (MR), X-ray processes or the like, it is frequently necessary for the patient who is to be examined to hold his or her breath while the image is being recorded, in order to avoid image artifacts caused by breathing movements. For this purpose, a breathing command is passed to the patient before the image is recorded, for example "breathe in—breathe out—breathe in—hold breath". The breathing command can be produced in an automated fashion from a memory via an appropriate voice output, which emits the stored text via a loudspeaker into the patient area and, for example, is fitted in the gantry of a CT system. When the examination process starts, the breathing command is started automatically, and the image recording is delayed until the breathing command has been completed, and the patient is holding his or her breath.

During an examination using contrast agent, a contrast agent pump can be activated in addition to the breathing command at the start of the examination process. The contrast agent is typically injected intravenously before or during the image recording, with the image recording being started as soon as the contrast agent is in the examination area. In order to keep the radiation dose low, the irradiation for image recording is delayed for a so-called circulation time, during which the contrast agent is transported to the examination area. By way of example, one such process is disclosed in DE 198 11 349 C1.

In the case of perfusion examinations, an automated breathing command is particularly important, since the patient has to hold his or her breath for a relatively long time, for example of more than 40 seconds, and the examination is therefore "corrupting by breathing" without a good initial breathing control, and can therefore no longer be evaluated. Owing to the relatively high radiation load involved with a CT perfusion examination, for example of 1 scan per second over 40 seconds, repetition resulting from problems of time coordination should be avoided in all circumstances. Furthermore, as little contrast agent as possible should be given, in order to minimize adverse health effects of the contrast agent. Since perfusion examinations are typically carried out closely related in time to other CT examinations, in which contrast agent must likewise be used, it is impossible to repeat the examination, since this would result in the maximum permissible daily dose being exceeded.

SUMMARY

In at least one embodiment of the invention, a control apparatus for a medical examination apparatus is disclosed, by which comprehensive breathing commands can be automated in order in this way to allow the examination images that are produced to be evaluated reliably.

A control apparatus, according to at least one embodiment of the invention, includes a control unit for controlling the start of the injection after the start of the breathing command. The procedure for perfusion processes, for example, can also be automated for breathing commands of different length, and can be made considerably simpler for an operator. Error sources resulting from manual control can be avoided, therefore allowing the examination to be carried out reliably.

At least one embodiment of the invention is based on the idea that the circulation time for perfusion examinations is short, lasting for only a few seconds, since the aim is not only to make the examination area visible, but also to make the flow of contrast agent fully visible. In examinations such as these, the circulation time therefore ends before the contrast agent has reached the examination area. It may therefore be the time between the start of injection and the contrast agent reaching the examination area, or some other shorter time, which is used for the contrast agent to be transported in the direction of the examination area, without it reaching the examination area, in order to make it possible to observe the contrast agent entering and flowing through this area.

It is also worthwhile starting the image recording even before the contrast agent arrives in the examination area in order to obtain at least one image that is free of contrast agent. This makes it possible to observe the contrast agent entering and subsequently flowing away from this area, thus making it possible to deduce characteristics of the examination area. For examinations such as these, the circulation time is normally set to 4 seconds. However, an expedient breathing command for examinations of this type lasts for eight or more seconds, in order to achieve blood oxygen saturation and therefore to allow the breath to be held reliably for a long time during the examination.

It is helpful for the operator of the examination apparatus for him or her to be able to start the examination process and not to have to take any more action, for example to operate the contrast agent injector. Operator errors can be avoided by a single start command, and the process can be carried out reliably. However, if the examination process is started at a single command, then the breathing command starts at the same time as the start command for the contrast agent injector, which waits for the selected circulation time, and then injects the contrast agent. If the breathing command is long, it is not complete until the contrast agent has actually arrived in the examination area. If the image recording does not start until this time, then it is no longer possible to observe the agent entering the examination area. If the image recording starts prior to this, then the start of image recording can be affected by breathing by the end of the breathing command.

If the start of the first injection of contrast agent is, according to at least one embodiment of the invention, delayed with respect to the breathing command, that is to say it is started after the start of the breathing command, then the circulation time can be set independently of the duration of the breathing command, for example to a short time period, and the image recording can be delayed until the breathing command has ended. The injection starts only after the delay, so that the circulation time expediently ends only at or after the end of the breathing command. The process can be started simply by a single command, and images which can be evaluated reliably can be achieved.

The injection of contrast agent is the first injection for the examination, so that it is not preceded by any test bolus or the like. The first contrast agent is injected after a time which is free of contrast agent and lasts for at least five minutes, in order to ensure that the examination area is at least largely free of contrast agent before the examination, expediently after a time free of contrast agent lasting for at least one hour. At least one embodiment of the invention is suitable for all examinations carried out with contrast agent, in particular as an additional option for short circulation times and/or long breathing commands.

The breathing command is advantageously produced automatically, for example from a tape or a data storage medium. Its length is therefore known. However, it is possible for an operator to select different breathing commands, for example in different languages and those in which the breathing is held after inspiration, as well as those in which the breathing is held after expiration. The duration of the breathing command is therefore not always the same, depending on the selected breathing command. In order to determine the time for starting the injection or the duration of the delay as appropriate for each breathing command, the time at which the injection is started is expediently chosen as a function of the length of the breathing command. One particularly simple relationship is provided if the control unit is provided in order to determine a delay time for the injection from the difference between the duration of the breathing command and the circulation time.

If the breathing command is long, examination can be carried out quickly, if the control unit is provided in order to control the start of the breathing command immediately after a start signal has been entered by an operator.

In a further advantageous refinement of at least one embodiment of the invention, the control unit is provided in order to process an entered circulation time independently of the length of the breathing command. The independence of the two variables allows the examination to be carried out flexibly and reliably. Any time difference between the length of the breathing command and the circulation time can be compensated for by the delay. The control unit is advantageously provided in order to output the circulation time, for example to a contrast agent injector, which autonomously controls the injection.

If the output unit is provided in order to control the start of an injection as a function of a breathing command parameter, for example its duration, then the start of injection can be automated, and can be controlled reliably, for example on the basis of the start of the breathing command.

The control unit is advantageously provided in order to determine a delay time in addition to the circulation time. This allows the delay according to at least one embodiment of the invention to be achieved easily, and to be controlled by different control units. For example, the delay time can be emitted to a control unit for the contrast agent injection, which autonomously controls the start of injection.

A high degree of flexibility for the control apparatus can be achieved if the control unit is provided in order to process different breathing command lengths. Breathing commands in different languages and with different breathing parameters can be stored and processed, in which case the start of an injection can be controlled automatically as a function of the respective breathing command length.

If the breathing command length is longer than the circulation time, then the delay is advantageously first of all controlled for the start of a process for a perfusion examination, rather than starting the injection immediately, as was previously normal. In order to inform the operator of this, it is advantageous for the control unit to be provided in order to output operator information if the breathing command length is greater than the circulation time.

A further object of at least one embodiment of the invention is an imaging medical examination apparatus having a control apparatus as described above.

If the examination apparatus is equipped with a contrast agent injector with a control unit for checking and processing a delay time in addition to the circulation time, the delay time determined by the control apparatus can be processed further by the control unit in order to autonomously control the start of the injection.

BRIEF DESCRIPTION OF THE DRAWINGS

The invention will be explained in more detail with reference to example embodiments, which are illustrated in the drawings, in which FIG. 1 shows a computed-tomography scanner with a contrast agent injector, and FIG. 2 shows a timing procedure for an examination process.

DETAILED DESCRIPTION OF THE EXAMPLE EMBODIMENTS

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described. Like numbers refer to like elements throughout. As used herein, the terms "and/or" and "at least one of" include any and all combinations of one or more of the associated listed items.

FIG. 1 shows, schematically, an examination apparatus 2, which is in the form of a computed-tomography scanner, with a gantry 4 which accommodates an imaging apparatus 6 with a radiation unit 8, a detector unit 10 and a breathing command transmitter 12 with a loudspeaker 14. Together with the radiation unit 8, the detector unit 10 and the loudspeaker 14, a control apparatus 16 is connected to a control unit 18, which is additionally connected to an input device 20 in the form of a keyboard and mouse for example, to an output device 22 in the form of a screen for example, and to a contrast agent injector 24. The contrast agent injector 24 itself has a control unit 26, which is part of the control apparatus 16, a contrast agent pump 28 and an injection device 30 in the form of a cannula connected to the contrast agent pump 28 for example. The cannula is injected into a patient 34, who is lying on a couch 32, in order to transfer the contrast agent through the patient's 34 circulation to an examination area 36 in the patient's 34 brain.

FIG. 2 shows a time procedure for an examination process carried out using the examination apparatus 2. In order to examine the patient 34, an operator, for example a medical-technical assistant, uses the keyboard and a menu 38 displayed on the screen to enter a circulation time $\Delta t_{Kr}$, which is the minimum time that should be waited for after the start of the injection $t_I$ before recording should be started $t_B$, at which time image recording is started. The circulation time $\Delta t_{Kr}$ is set such that the image recording can observe the contrast agent entering the examination area 36. In addition, the operator selects a breathing command AK with a command length $\Delta t_A$, by selecting the nature and language for the breathing command AK, using a menu 38. The control apparatus 16 is provided in order to process the input circulation time $\Delta t_{Kr}$ independently of the command length $\Delta t_A$, and does not lengthen the circulation time $\Delta t_{Kr}$ despite the long command length $\Delta t_A$.

If the circulation time $\Delta t_{Kr}$ is greater than the command length $\Delta t_A$ then there are no special features for the time coordination of the examination process, and the breathing command AK may be started, for example, at the same time as the injection I. However, in the following example embodiment, the operator has selected a 4-second circulation time $\Delta t_{Kr}$ and a command length $\Delta t_A$ of 9 seconds. The control unit 18 uses this data in a process step 42 to calculate a delay time $\Delta t_v$, using the simple relationship $\Delta t_v = \Delta t_A - \Delta t_{Kr}$, on the basis on which it controls the start of injection $t_I$ as a function of the command length $\Delta t_A$.

Since the breathing command AK is longer than the circulation time $\Delta t_{Kr}$, the control unit 18 emits operator information 40 on the output device 22 in a method step 44, informing the operator that the command length $\Delta t_A$ of the breathing command AK is longer than the circulation time $\Delta t_{Kr}$, and thus that the first injection I of contrast agent will be started with a delay time of $\Delta t_v$ with respect to the breathing command AK. The operator information also informs the operator that he should not enter the start command on the contrast agent injector 24, since it does not know the delay time $\Delta t_v$, and it would then not be possible to carry out the entire length of the breathing command AK. In a somewhat more convenient embodiment of the examination apparatus 2, the operator information 40 informs the operator that a start button on the contrast agent injector 24 is blocked, or has been rendered inoperative, in order to ensure that the long breathing command AK is played back completely. The operator information 40 is configured particularly strikingly as a pop-up window, but may also be configured in a different form.

After matching of the control units 18, 26, a starting means associated with the control unit 18, for example a keyboard command, is enabled. The operator now gives a start command at the start time $t_s$. In one simple embodiment of the examination apparatus 2, the timing of the examination is coordinated solely by the control unit 18, which also coordinates the image recording. In response to the start signal, the control unit 18 controls the start $t_A$ of the breathing command API, which is then passed to the patient 34 in an audible form via the loudspeaker 14. 5 seconds after the command start $t_A$, that is to say once the delay time $\Delta t_v$ has elapsed, the control unit 18 sends an appropriate signal to the control unit 26, that sends this to the contrast agent pump 28, which now starts to inject I the contrast agent, at the injection start $t_I$.

During the circulation time $\Delta t_{Kr}$ of 4 seconds, the breathing command AK and the contrast agent pump are active at the same time until, after the end of the breathing command AK, image recording is started at the recording start $t_B$. The time in which the contrast agent is injected I is independent of the start $t_B$ of image recording. It lasts for a total of eight seconds, with a saline solution being subsequently injected in addition for four seconds after this time, maintaining the flow of contrast agent, by "moving on the contrast agent". The contrast agent reaches the examination area 36 about 1 second after the start of recording $t_B$, such that the first recorded examination image shows the examination area 36 without contrast agent.

Depending on the embodiment of the examination apparatus 2, in particular the contrast agent injector 24 and an interface between the control units 18, 26, minor modifications of the examination process are advantageous. For example, after the start time $t_s$, the control unit 18 can autonomously transmit the delay time $\Delta t_v$ to the control unit 26 for the contrast agent injector 24, which autonomously controls the start of injection $t_I$. If the contrast agent injector 24 is appropriately designed, it is likewise feasible for the operator to enter the start command on the contrast agent injector 24. This possibility is taken into account, of course, in the operator information 40. The contrast agent injector 24 checks during the matching process, which was previously carried out between the control units 18, 26, for the presence of a delay time $\Delta t_v$, which the control unit 18 transmits to the control unit 26. In response to the start signal from the operator, the control unit 26 controls the delay time $\Delta t_v$ autonomously, and initiates activity of the contrast agent pump 28 only after the delay time $\Delta t_v$ has elapsed, with the contrast agent pump 28 now starting to inject I the contrast agent at the injection start $t_I$.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A control apparatus for a medical examination apparatus, the control apparatus comprising:
   a control unit including a processor and a memory with computer-readable instruction stored thereon, which when executed by the processor, cause the processor to:
      control a breathing command,
      determine a delay time for an injection of a contrast agent for performing a medical examination of an examination area of a patient, from a difference between a duration of the breathing command and a circulation time, the delay time being a time after the start of the breathing command and before the injection, the injection of the contrast agent being the first injection for the examination, the circulation time being less than or equal to the duration of the breathing command and the circulation time being a time after a start of the injection until a time just before the contrast agent reaches the examination area, the examination not preceded by any injection of a test bolus,
      control the start of the injection based on the determined delay time, and
      control a recording of an examination image of the examination area of the patient after the circulation time has elapsed.

2. The control apparatus as claimed in claim 1, wherein the processor is configured to control the start of the breathing command immediately after a start signal has been entered by an operator.

3. The control apparatus as claimed in claim 1, wherein the processor is further configured to process the circulation time, independently of a length of the breathing command.

4. The control apparatus as claimed in claim 1, wherein the processor is configured to control Rail the start of an injection as a function of a breathing command parameter.

5. The control apparatus as claimed in claim 1, wherein the processor is further configured to receive the circulation time.

6. The control apparatus as claimed in claim 1, wherein the processor is further configured to process a plurality of individual breathing commands.

7. The control apparatus as claimed in claim 6, wherein the processor is further configured to output operator information when a command length of one of the plurality of individual breathing commands is greater than the circulation time.

8. The control apparatus as claimed in claim 1, wherein the medical examination apparatus is an imaging medical examination apparatus.

9. A control apparatus for a medical examination apparatus, the control apparatus comprising:
   a control unit including a processor and a memory with computer-readable instruction stored thereon, which when executed by the processor, cause the processor to:
   determine a delay time for an injection of a contrast agent for performing a medical examination of an examination area of a patient, from a difference between a duration of a breathing command and a circulation time, the delay time being a time after the start of the breathing command and before the injection, the injection of the contrast agent being the first injection for the examination, the circulation time being less than or equal to the duration of the breathing command and the circulation time being a time after a start of the injection until a time just before the contrast agent reaches the examination area, the examination not preceded by any injection of a test bolus; and
   control the start of the injection of the contrast agent based on the determined delay time.

* * * * *